United States Patent [19]

Aoki et al.

[11] 4,149,893

[45] Apr. 17, 1979

[54] ORTHOPEDIC AND DENTAL IMPLANT CERAMIC COMPOSITION AND PROCESS FOR PREPARING SAME

[75] Inventors: Hideki Aoki, Funabashi; Kazuo Kato; Tsuneo Tabata, both of Tokyo; Makoto Ogiso, Musashino, all of Japan

[73] Assignee: Tokyo Medical and Dental University, Tokyo, Japan

[21] Appl. No.: 740,776

[22] Filed: Nov. 10, 1976

[30] Foreign Application Priority Data

Nov. 21, 1975 [JP] Japan .................. 50-139328

[51] Int. Cl.² ............................................. C09K 3/00
[52] U.S. Cl. .......................................... 106/35; 32/15; 106/63
[58] Field of Search .................. 423/308; 106/35, 63; 32/15

[56] References Cited

U.S. PATENT DOCUMENTS

| | | | |
|---|---|---|---|
| 2,658,832 | 11/1953 | De Ment | 106/35 |
| 3,379,541 | 4/1968 | Tuvell | 106/38.27 |
| 3,787,900 | 1/1974 | McGee | 106/35 |

*Primary Examiner*—Lorenzo B. Hayes
*Attorney, Agent, or Firm*—Armstrong, Nikaido, Marmelstein & Kubovcik

[57] ABSTRACT

Disclosed is an orthopedic and dental implant ceramic composition comprising hydroxyapatite and whitlockite. Said composition is prepared by blending 50 to 99.5% by weight of a crystalline hydroxyapatite and 0.5 to 50% by weight of whitlockite, and then, sintering the blend at a temperature of 900° to 1,400° C. Said crystalline hydroxyapatite is prepared by the solid phase reaction wherein a mixture of a calcium phosphate, having a Ca/P ratio of 1.5 to 1.67 by mole, and a stoichiometric amount or more of a calcium compound is heated at a temperature of 500° to 1,000° C. Said calcium compound is at least one compound selected from the group consisting of $CaCO_3$, $CaO$, $Ca(OH)_2$, $CaF_2$, $Ca(COO)_2$, $Ca(NO_3)_2$ and $CaCl_2$.

5 Claims, 2 Drawing Figures

ORTHOPEDIC AND DENTAL IMPLANT CERAMIC COMPOSITION AND PROCESS FOR PREPARING SAME

BACKGROUND OF THE INVENTION

The invention relates to a polycrystalline ceramic composition usable for artificial prostheses in orthopedic and dental fields, and to a process for the preparation thereof.

Recently, it has been earnestly desired to develop new implant materials which can be safely buried in a human or animal body as a prosthesis for a bone or tooth damaged by an accident or by a disease such as bone tumor, dental caries or serious periodontic disease, and intimately bound to a vital tissue without any rejection phenomena so that the functions thereof are maintained for a long period of time.

Various metallic and organic materials have hitherto been used as an implant material for a bone or tooth in the orthopedic and dental fields. However, the metallic and organic materials have various drawbacks and, thus, are not satisfactory as a prosthesis in a human or animal body. On the other hand, ceramics of inorganic substances are stable in a human or animal body and have excellent affinity for a human or animal body, and therefore, they are becoming one of the most useful materials as a prosthesis in the orthopedic and dental fields. Recently, ceramics such as bioglasses of an $SiO_2$—$Na_2O$—$CaO$—$P_2O_5$ type, vitreous carbons and $Al_2O_3$ have been practically utilized as an implant material for a bone or tooth. However, these conventional artificial ceramic materials have drawbacks in that they are not bound chemically to a vital tissue and, thus, are only retained permanently in the body as an alien material.

Hydroxyapatite, which is represented by the formula $Ca_5(PO_4)_3OH$ and is one of the calcium phosphates, constitutes a main component of the minerals of bones and teeth. Thus, for the last two or three years, ceramics based on hydroxyapatite have increasingly become of great interest in the orthopedic and dental fields. For example, publicly disclosed Japanese Patent Application No. 51-40400 discloses the use and production of a polycrystalline ceramic based on hydroxyapatite. According to this prior art, the polycrystalline ceramic is obtained by reacting a calcium ion and a phosphate ion in an aqueous medium, separating the resulting gelatinuous precipitate of calcium phosphate of a Ca/P ratio between 1.5 and 1.67 by mole from the aqueous medium and calcining the gelatinuous precipitate. In this art, however, it is troublesome to separate the gelatinuous calcium phosphate from the aqueous medium because the separation must be very carefully carried out.

The Ca/P ratio by mole of the gelatinuous calcium phosphate is changed with the lapse of time (see H. Aoki, Reports of the Institute for Medical & Dental Engeneering, No. 7, pages 107 through 111 (1973)). Accordingly, it is difficult to maintain the Ca/P ratio by mole of the gelatinuous calcium phosphate constant for a long time and, thus, it is impossible to preserve the gelatinuous calcium phosphate for a long time as a starting material which is always usable for the calcination. Further, if the hydroxyapatite obtained by heating the gelatinuous calcium phosphate from the aqueous solution reaction is heated to a temperature above 1,250° C., the hydroxyapatite is partially decomposed into whitlockite. Thus, it is difficult to obtain a product having a constant composition.

SUMMARY OF THE INVENTION

It is the principal object of the present invention to provide an orthopedic and dental implant ceramic composition which can avoid the above-mentioned drawbacks encountered with the conventional implant materials and a process for the preparation thereof.

Thus, the invention provides an orthopedic and dental implant ceramic composition which comprises hydroxyapatite ($Ca_5(PO_4)_3OH$) and whitlockite ($Ca_3(PO_4)_2$) and which is prepared by blending 50 to 99.5% by weight of a crystalline hydroxyapatite, being prepared by the solid phase reaction wherein a mixture of a calcium phosphate having a Ca/P ratio of 1.5 to 1.67 by mole and a stoichiometric amount or more of at least one calcium compound selected from the group consisting of $CaCO_3$, $CaO$, $Ca(OH)_2$, $CaF_2$ and $CaCl_2$ is heated at a temperature of 500° to 1,000° C., and 0.5 to 50% by weight of whitlockite and, then, sintering the blend at a temperature of 900° to 1,400° C.

The above and other objects and features of the invention will be clear from the reading of the ensuing detailed description of the invention with reference to the accompanying drawings.

DETAILED DESCRIPTION OF THE INVENTION

Figures 1A, 1B, 1C, 1D, 1E:
FIGS. 1a through 1e are photographs showing the reversed positive images of the X-ray photographic images illustrating the states of artificial tooth roots made of sintered apatite of various compositions and of gold in a tooth extraction fovea of a dog after two months from the time when they have been buried in the fovea.

The crystalline hydroxyapatite usable as a starting material for the preparation of the orthopedic and dental implant ceramic composition of the invention may be prepared by the solid phase reaction of a calcium phosphate having a Ca/P ratio of 1.5 to 1.67 by mole and a stoichiometric amount or more of a calcium compound at a temperature of 500° to 1,000° C. The solid phase reaction may be carried out in the air or steam. If a stoichiometrically excess of the calcium compound is used, the resulting hydroxyapatite should be washed with water or an aqueous $NH_4Cl$ solution to remove the excessive calcium compound. This solid phase reaction according to the invention makes it possible to produce hydroxyapatite which is stoichiometrically pure and has a very excellent sinterability. The obtained hydroxyapatite is very thermostable so that it is not decomposed at all even if it is heated to a high temperature of 1,400° C.

In the preparation of the ceramic composition of the invention, the blend of crystalline hydroxyapatite and whitlockite may preferably be dressed into a grain size of 20 to 300 mesh before the sintering. Before or during the sintering, the blend of crystalline hydroxyapatite and whitlockite is formed into a desired shape by press molding. Where the press molding is to be carried out before the sintering, this may be effected using a mold press or a rubber press, preferably under a pressure of 500 to 5,000 kg/cm². Then, the molded article is sintered at a temperature of 900° to 1,400° C., for 10 minutes to 10 hours, preferably in the air or an inert gas such as $N_2$, $CO_2$, helium or argon. Where the press molding is to be carried out during the sintering, this may be effected by hot press sintering at a temperature of 900° to 1,400° C., under a pressure of 50 to 5,000 kg/cm², preferably 50 to 1,000 kg/cm², for 1 minute to 5 hours.

Before the sintering, if desired, at least one compound selected from the group consisting of MgO, $Na_2O$, $K_2O$, $CaF_2$, $Al_2O_3$, $SiO_2$, $Fe_2O_3$, $MnO_2$, ZnO and C may be added to the blend of crystalline hydroxyapatite and whitlockite in an amount of 0.1 to 45% based on the weight of the blend of crystalline hydroxyapatite and whitlockite.

The ceramic composition of the invention is very dense having a density corresponding to 55% to approximately 100% to the theoretical density. The ceramic composition has good strength. For example, columns of a diameter of 1 cm and a length of 1 cm, obtained by compression molding of a blend of crystalline hydroxyapatite and whitlockite containing 45% by weight of whitlockite and then sintering the molded article at a temperature ranging from 1,000° to 1,300° C., have been proved to have a compressive strength of about 2 to 10 times that of columns obtained from only the crystalline hydroxyapatite in the same manner. Also, the ceramic composition of the invention has very excellent affinity for vital tissues. If an artificial tooth root made of the composition is buried in a tooth extraction fovea of a dog, the artificial tooth root is strongly fixed in the fovea while soft parts become glued to the artificial tooth root and, further, bone becomes newly formed around the surface of the artificial tooth root within two or three weeks. A test for solubility in distilled water has proved that whitlockite ($Ca_3(PO_4)_2$) has a solubility of about 10 times that of hydroxyapatite. Thus, it may be presumed that if the ceramic composition of the invention is planted in a human or animal body, whitlockite is smoothly dissolved, and this accelerates the formation of bone around the planted composition.

It is possible to make the resulting composition in a glass state where the blend of hydroxyapatite and whitlockite containing $SiO_2$ and $Na_2O$ is sintered. This is an advantage because the composition can easily be formed into a desired shape. In the ceramic composition of the invention, $K_2O$ may advantageously act to make the resulting composition in a glass state, MgO and C may be effective to increase the flexural strength of the composition and $CaF_2$ and $Al_2O_3$ may be effective to increase the mechanical strength and heighten the hardness of the composition. ZnO, $MnO_2$ and $Fe_2O_3$ may be effective to make it possible to sinter the composition in a wide temperature range.

Further, as hereinbefore mentioned, the crystalline hydroxyapatite usable as a starting material in the invention is stoichiometrically pure and has very excellent sinterability and thermostability. Thus, the resulting ceramic composition becomes very dense, has a high strength and can have a desired composition of hydroxyapatite and whitlockite depending upon the amounts of the used hydroxyapatite and whitlockite. The crystalline hydroxyapatite is not contracted very much when molded and sintered and, thus, can give a desired exact size to the final shaped article.

The ceramic composition of the invention may advantageously be used as an implant material in the orthopedic and dental fields in forms of molded and sintered articles. However, it may also be used as an implant material wherein the composition is coated onto the surface of a shaped support of an appropriate substrate.

The invention will be further illustrated by the following illustrative, but not limitative, examples.

EXAMPLE 1

To 1 l of a 0.3 mol/l aqueous solution of $Na_2HPO_4$, 16 g of granular NaOH was added and, then, a 0.5 mol/l aqueous solution of $CaCl_2$ was slowly added dropwise with stirring. The mixture was then reacted at 25° C. and a pH value of 8 to 9 for 24 hours to obtain a calcium phosphate having a Ca/P ratio of 1.5 to 1.6 by mole. The obtained calcium phosphate was washed with water, filtered and, then, dried into a microcrystalline powder. The calcium phosphate powder was blended with $Ca(OH)_2$ in a molar ratio of 2:1 and, then, they were reacted at 900° C. for 1 hour in the air to produce hydroxyapatite.

The X-ray diffraction of the obtained hydroxyapatite proved that it was pure and had a very high crystallinity. The precise calculation of the lattice constant showed that a was 9.408±0.001 A, c was 6.875±0.002 A and V was 527.0±0.2 A³, and proved that the obtained hydroxyapatite had a fairly shorter a-axis and was a crystalline body having a higher density of 3.16 g/cm³, as compared with hydroxyapatite formed conventionally from a solution or with natural apatite. The Ca/P ratio by mole determined by atomic-absorption spectroscopy and colorimetry was 1.67, which corresponds to the calculated value. The hydroxyapatite was thermostable so that it was not decomposed at all even by being heated to a high temperature of 1,400° C.

EXAMPLE 2

55 parts by weight of the hydroxyapatite produced in Example 1 were blended with 45 parts by weight of whitlockite by grinding in a mortar. The grain size of the ground mixture was dressed into 250 mesh. Then, 2 g of the mixture was press molded, under 1,000 kg/cm² for 3 minutes, into a column of a diameter of 10 mm and a length of 7 mm. The column was then sintered in the air at 1,350° C. for 1 hour.

The sintered product thus obtained was opaque and dense and had a density corresponding to 97% of the theoretical density, a compressive strength of 2,500 kg/cm² and a flexural strength of 700 kg/cm².

EXAMPLES 3 THROUGH 15

By repeating the procedure in Example 2, but using each starting material having the composition as shown in Table 1 below, sintered columns of the same size were obtained. However, MgO and $Al_2O_3$ was used in a form of whisker of a diameter of about 1μ and a length of about 10μ and C was used in a form of fiber of the same size.

Table 1

| Example No. | $Ca_5(PO_4)_3OH$ | $Ca_3(PO_4)_2$ | MgO | $Na_2O$ | $K_2O$ | $CaF_2$ | $Al_2O_3$ | $SiO_2$ | $Fe_2O_3$ | $MnO_2$ | ZnO | C |
|---|---|---|---|---|---|---|---|---|---|---|---|---|
| 3 | 95 | 5 | | | | | | | | | | |
| 4 | 50 | 45 | 2.8 | 1.0 | 1.0 | 0.2 | | | | | | |
| 5 | 90 | 7 | 0.8 | 1.8 | 0.2 | 0.2 | | | | | | |
| 6 | 85 | 5 | 10 | | | | | | | | | |
| 7 | 90 | 5 | 5 | | | | | | | | | |
| 8 | 85 | 5 | | | | | 10 | | | | | |
| 9 | 90 | 5 | | | | | 5 | | | | | |
| 10 | 85 | 5 | | | | | | 10 | | | | |
| 11 | 90 | 5 | | | | | | 5 | | | | |
| 12 | 85 | 5 | | | | | | | 10 | | | |
| 13 | 85 | 5 | | | | | | | | 10 | | |
| 14 | 85 | 5 | | | | | | | | | 10 | |
| 15 | 85 | 5 | | | | | | | | | | 10 |

The determination of compressive strength of the products proved that the product of Examples 6 and 7 was the strongest, being 4,000 kg/cm², the product of Examples 8 and 9 had a compressive strength of 3,500 kg/cm², the product of Example 5 had a compressive strength of 3,000 kg/cm² and the other products had a compressive strength of 2,500 to 3,000 kg/cm². All of the products had a flexural strength of 800 to 1,000 kg/cm² and a density of 85 to 95% of the theoretical density.

COMPARATIVE EXAMPLE

The procedure in Example 2 was repeated, but without using the whitlockite. Thus, a sintered column of the same size was obtained.

The product had a density corresponding to 95% of the theoretical density and had a compressive strength of 1,500 kg/cm², which corresponds to about ½ of the strength of the product of Example 2.

EXAMPLE 16

Each of the starting materials having the compositions as in Examples 3, 4 and 5 was hot press sintered at 1,300° C. under 200 kg/cm² for 1 hour. The obtained products were transparent and had a compressive strength of about 5,000 kg/cm² and a flexural strength of about 1,200 kg/cm².

EXAMPLE 17

Columns obtained as in Examples 3, 4 and 5 and as in Comparative Example, as well as a gold column of the same size, were buried in a tooth extraction fovea of a dog as an artificial tooth root. An adult dog was anesthetized and the first molar of the mandible of the dog was extracted. Immediately after the extraction, the column was buried in the fovea. The buried columns were observed by X-ray photography.

FIGS. 1a through 1e respectively correspond to the products of Examples 3, 4 and 5, Comparative Example and of gold. As is seen from FIGS. 1a through 1d, in the proximity of the upper ends of the products of Examples 3, 4 and 5, and Comparative Example, strong transmission images are observed, which proves that these products broadly absorbed bone and, thus, were strongly fixed to the vital tissue. Contrary to this, FIG. 1e shows that the product of gold had no affinity for the vital tissue.

Figure 2:
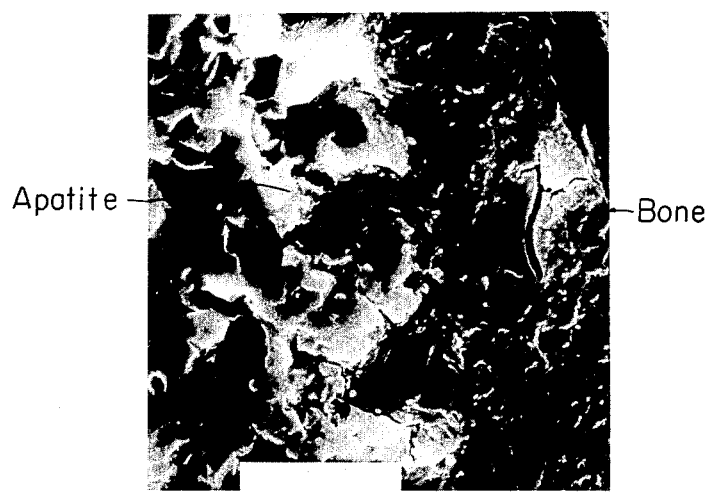
FIG. 2 is a micrograph by a scanning electron microscope by 2,400 X magnification showing the bonding state of an artificial tooth root according to the invention to the vital tissue of a dog after three months from the time when it has been buried in the tooth extraction fovea.

FIG. 2 shows the bonding state of the product of Example 3 to the vital tissue after three months from the time it was buried in the tooth extraction fovea of the dog. This figure proves that this product was intimately bound to the newly formed bone.

EXAMPLE 18

Four columns obtained in a manner similar to that in Example 3 and respectively having densities of 55, 65, 75 and 85% of the theoretical density were tested as described in Example 17.

It was observed that within two months, bone was formed around the surfaces of all of the columns. Especially, around the surface of the column having a density of 85%, bone was formed within two weeks.

What is claimed is:

1. An orthopedic or dental implant ceramic composition comprising hydroxyapatite and whitlockite, said composition being prepared by blending 50 to 99.5% by weight of a crystalline hydroxyapatite and 0.5 to 50% by weight of whitlockite, and then, sintering the blend at a temperature of 900° to 1,400° C.; said crystalline hydroxyapatite being prepared by the solid phase reaction wherein a mixture of a calcium phosphate, having a Ca/P ratio of 1.5 to 1.67 by mole, and a stoichiometric amount or more of a calcium compound is heated at a temperature of 500° to 1,000° C.; said calcium compound being at least one compound selected from the group consisting of $CaCO_3$, CaO, $Ca(OH)_2$, $CaF_2$, $Ca(COO)_2$, $Ca(NO_3)_2$ and $CaCl_2$.

2. A composition according to claim 1, wherein at least one compound selected from the group consisting of MgO, $Na_2O$, $K_2O$, $CaF_2$, $Al_2O_3$, $SiO_2$, $Fe_2O_3$, $MnO_2$, ZnO and C is further contained, added to the blend of hydroxyapatite and whitlockite in an amount of 0.1 to 45% based on the weight of said blend of hydroxyapatite and whitlockite.

3. A process for preparing an orthopedic and dental implant ceramic composition, which comprises blending 50 to 99.5% by weight of a crystalline hydroxyapatite and 0.5 to 50% by weight of whitlockite, and then, sintering the blend at a temperature of 900° to 1,400° C., said crystalline hydroxyapatite being prepared by the solid phase reaction wherein a mixture of a calcium phosphate having a Ca/P ratio of 1.5 to 1.67 by mole and a stoichiometric amount or more of a calcium compound is heated at a temperature of 500° to 1,000° C.; said calcium compound being at least one compound selected from the group consisting of $CaCO_3$, CaO, $Ca(OH)_2$, $CaF_2$, $Ca(COO)_2$, $Ca(NO_3)_2$, and $CaCl_2$.

4. A process according to claim 3, wherein at least one compound selected from the group consisting of MgO, $Na_2O$, $K_2O$, $CaF_2$, $Al_2O_3$, $SiO_2$, $Fe_2O_3$, $MnO_2$, ZnO and C is added to the blend of hydroxyapatite and whitlockite in an amount of 0.1 to 45% based on the weight of said blend of hydroxyapatite and whitlockite before the sintering.

5. A process according to claim 3, wherein the blend of hydroxyapatite and whitlockite is dressed into a grain size of 20 to 300 mesh.

* * * * *